United States Patent [19]

Hanson et al.

[11] 4,393,241

[45] Jul. 12, 1983

[54] SYNTHESIS OF ALKOXY AND PHENOXY SUBSTITUTED ARYL SULFIDES

[75] Inventors: Harry T. Hanson, Millburn, N.J.; John B. Sapp, Jr., Houston, Tex.

[73] Assignee: Celanese Corporation, New York, N.Y.

[21] Appl. No.: 344,337

[22] Filed: Feb. 1, 1982

[51] Int. Cl.$^3$ ............................................. C07C 149/32
[52] U.S. Cl. ........................................ 568/49; 528/381
[58] Field of Search ..................... 568/48, 49; 528/381

[56] References Cited

U.S. PATENT DOCUMENTS

| | | | |
|---|---|---|---|
| 2,139,321 | 12/1938 | Mikeska et al. | 568/48 |
| 2,299,213 | 10/1942 | Cook et al. | 568/48 |
| 2,370,756 | 3/1945 | Sibley | 568/58 |
| 2,402,685 | 6/1946 | Signaigo | 568/21 |
| 2,971,968 | 2/1961 | Nicholson et al. | 260/439 |
| 3,057,926 | 10/1962 | Coffield | 568/23 |
| 3,129,213 | 4/1964 | Worrel | 260/137 |
| 3,718,699 | 11/1977 | Fujisawa et al. | 568/23 |
| 4,056,568 | 11/1977 | Cisney | 568/48 |
| 4,178,433 | 12/1979 | Smith | 528/381 |

FOREIGN PATENT DOCUMENTS 1213677  11/1970  United Kingdom .................. 568/49

Primary Examiner—Donald G. Daus
Assistant Examiner—M. C. Eakin
Attorney, Agent, or Firm—Burns, Doane, Swecker & Mathis

[57] ABSTRACT

Provided is a novel process for the synthesis of aryl sulfides substituted with an alkoxy or phenoxy substituent. The process comprises reacting an alkoxy or phenoxy substituted aromatic compound with a sulfur dihalide, preferably sulfur dichloride, in the presence of an alkali metal tetrafluoroborate catalyst, with the amount of said aromatic reactant compound preferably being sufficient to solvate the sulfur dichloride and catalyst sufficiently to allow the reaction to occur.

17 Claims, No Drawings

SYNTHESIS OF ALKOXY AND PHENOXY SUBSTITUTED ARYL SULFIDES

BACKGROUND OF THE INVENTION

1. Field of the Invention

This invention relates to a process for the catalytic production of substituted aryl sulfides. More particularly, this invention relates to a process for the production of alkoxy and phenoxy substituted aryl sulfides, especially substituted diaryl sulfides, wherein an alkali metal tetrafluoroborate catalyst is employed.

2. Background of the Invention

A wide variety of aryl sulfides, and in particular diaryl sulfides and di(alkaryl) sulfides, are known, the utilities of which are just as varied. For example, aryl and in particular diaryl sulfides are known to be useful as intermediates, especially for the preparation of insecticides, as plasticizers, high boiling solvents, heat exchange fluids, and hydraulic fluids.

A well known class of substituted aryl sulfides is that of the hydroxy substituted diaryl sulfides, or thiobisphenols, same having utility as intermediates or as oxidation inhibitors. One generally known process for preparing hydroxy substituted diaryl sulfides, or thiobisphenols, is by reacting a phenol with a sulfur chloride compound.

For example, U.S. Pat. No. 4,056,568 discloses the reaction of a 3,5-dialkyl phenol with a sulfur chloride compound to form a sulfenyl chloride. Subsequent reaction thereof with a phenol produces a diaryl monosulfide.

U.S. Pat. No. 3,718,699 discloses a process of preparing 4,4'-dithiobis(2,6-di-t-butylphenol). Said process comprises reacting 2,6-di-t-butylphenol with sulfur monochloride in the absence or presence of a catalytic amount of iron powder or a Lewis acid.

U.S. Pat. No. 3,129,213 discloses a process wherein an orthoalkylphenol is reacted with sulfur dichloride to form a reaction product suitable for use as an antioxidant and anti-wear agent. U.S. Pat. No. 3,057,926 discloses a process wherein an alkyl or alkoxy substituted phenol is reacted with sulfur dichloride. Alternatively, the process may comprise the reaction of an alkali metal salt of the substituted phenol with sulfur dichloride. Neither reaction, however, is conducted in the presence of a catalyst.

Similarly, U.S. Pat. Nos. 2,139,321; 2,370,756; and 2,971,968 disclose the preparation of thiobisphenols by reacting an alkyl phenol with a sulfur chloride compound in the absence of a catalyst.

U.S. Pat. No. 2,402,685, however, discloses reacting a phenol with sulfur dichloride in the presence of a "sulfurization catalyst" to produce a diaryl monosulfide product. Examples of suitable "sulfurization catalysts" include aluminum chloride, bismuth chloride, iron chloride, mercuric chloride, tin chloride, antimony chloride, tantallum pentachloride, titanium tetrachloride and zinc chloride.

While numerous processes are known for preparing hydroxy substituted aryl sulfides, the prior art is devoid, however, of a truly suitable process for the formation of aryl sulfide compounds, and in particular diaryl sulfides, wherein the aromatic rings are substituted, particularly in the para positions, with a more complex electron releasing group, such as an alkoxy or phenoxy. Such a process, particularly if given to high reaction rates and yields, would find ready acceptance by the industry for the preparation of such compounds, which find utility as percursors, stabilizers, plasticizers, etc.

Accordingly, it is an object of the instant invention to provide a process for the effective and efficient preparation of alkoxy and phenoxy substituted aryl sulfides.

It is another object of the instant invention to provide a novel process for the preparation of substituted diaryl sulfides, and in particular, diaryl sulfides substituted in the para positions with an alkoxy or phenoxy substituent.

Still another object of the instant invention is to provide a process for preparing diaryl sulfides in high yields, with high reaction rates, and with high selectivity.

These and other objects, as well as the scope, nature and utilization of the invention, will be apparent to those skilled in the art from the following description and the appended claims.

SUMMARY OF THE INVENTION

It has now been unexpectedly and most surprisingly discovered that alkoxy and phenoxy substituted aryl sulfides can be produced at a high reaction rate and in good yields by reacting an aromatic compound of the structural formula

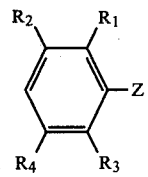

wherein $R_1$, $R_2$, $R_3$ and $R_4$, which can be the same or different, represent hydrogen or lower alkyl, i.e., from 1–6 carbon atoms, and Z is $-OR_5$ with $R_5$ representing an alkyl, preferably an alkyl having from 1 to 8 carbon atoms, or phenyl, with a sulfur dihalide in the presence of a catalytic amount of an alkali metal tetrafluoroborate catalyst. It is also preferred that when the aromatic compound reactant is a liquid at the reaction temperature, that an amount of said aromatic compound be employed sufficient to solvate the sulfur dihalide and catalyst sufficiently to allow said reacting to occur.

The process of the instant invention can be utilized to efficiently prepare either diaryl or oligomeric products. An oligomeric product, i.e., containing up to about 50 aryl units, is produced by employing a molar ratio of aromatic reactant to sulfur dihalide of greater than 1:1 but less than 2:1, whereas the substituted diaryl sulfides are obtained by employing a molar ratio of aromatic reactant compound to sulfur dihalide of about 2:1 or greater.

DETAILED DESCRIPTION OF THE INVENTION

The process of the instant invention provides one with a relatively fast, effective, and simple process for preparing alkoxy and phenoxy substituted aryl sulfides, and in particular, aryl sulfides substituted in the para positions.

In preparing diaryl sulfides, the process of the instant invention is essentially a coupling reaction which can be depicted schematically as follows:

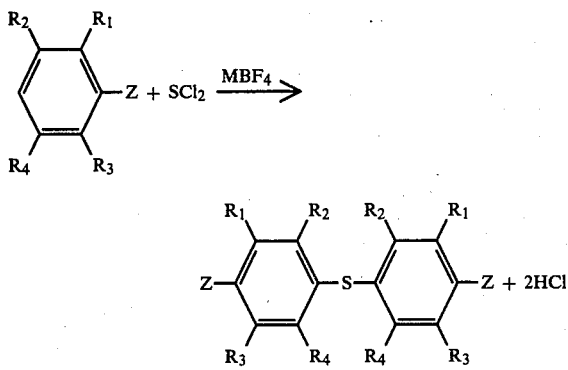

wherein $R_1$, $R_2$, $R_3$ and $R_4$, being either the same or different, represent a substituent which does not interfere or adversely affect the reaction, for example, hydrogen or a lower alkyl, i.e., an alkyl containing from 1 to 6 carbons, and Z is an alkoxy or phenoxy —$OR_5$ wherein $R_5$ represents an alkyl containing from 1 to 8 carbons, preferably from 1 to 4 carbons, or a phenyl, which may be substituted with an inert substituent, e.g., lower alkyl. It is preferable that $R_1$, $R_2$, $R_3$, $R_4$, being the same or different, are selected from the group consisting of hydrogen and methyl, and most preferably are all hydrogen.

Respecting the position para from the alkoxy or phenoxy substituent in the aromatic reactant compound of the instant process, said position always remains unsubstituted of any substituent which would adversely affect the possible reaction with sulfur at that position. This allows for one to take advantage of the para-coupling specificity of the instant process, as it has been found that the process of the instant invention exhibits near quantitative selectivity to the bis(p-substituted) diaryl sulfide product, as depicted in the above schematic.

Oligomers containing more than 2 aryl units and up to about 50 aryl units are produced, of course, when the coupling reaction is continued to produce a longer chain. The molar ratio of the aromatic reactant to sulfur dihalide reactant determines the product obtained, with diaryl products being produced quickly and effectively when the molar ratio is about 2:1 or greater and oligomers being produced generally when the molar ratio is greater than 1:1 but less than about 2:1.

A most preferred aromatic compound reactant for the process of the instant invention is anisole or diphenyl ether, i.e., wherein $R_5$ is methyl or phenyl respectively, as the instant process has been found most suitable for coupling anisole to form 4,4'-dimethoxydiphenyl sulfide and diphenyl ether to form 4,4'-diphenoxydiphenyl sulfide.

Other suitable aromatic compound reactants include 2-methylmethoxybenzene; 2,5-dimethylmethoxybenzene; ethoxybenzene; 3-methylethoxybenzene; 2,5-dimethylethoxybenzene; 2-ethylethoxybenzene; propoxybenzene; 2,3-dimethylpropoxybenzene; 3-butylpropoxybenzene; 2,5-diethylpropoxybenzene; n-butoxybenzene; 3,5-dimethyl-n-butoxybenzene; 3-methyldiphenyl ether; and 4,4'-dimethyldiphenyl ether.

It is preferred that the sulfur dihalide reactant employed be of high purity, e.g., containing less than 5 percent by weight of impurities. Such sulfur dihalides are commercially available. The most preferred sulfur dihalide for use in the process of the present invention is sulfur dichloride, which is an easily isolated, stable compound.

The reaction of the instant invention is necessarily conducted in the presence of a catalytic amount of an alkali metal tetrafluoroborate catalyst, as represented by $MBF_4$, with M representing an alkali metal. The preferred alkali metal tetrafluoroborate catalysts are those wherein the alkali metal is selected from the group consisting of lithium and sodium, with sodium tetrafluoroborate being the most effective catalyst in terms of yield and reaction rate, and thus, the most preferred catalyst. The alkali metal salts of tetrafluoroboric acid are well known, and are commercially available.

The amount of catalyst employed is generally any amount sufficient to effectively bring about a catalytic effect in the reaction, i.e., a catalytic amount. Although any effective amount of catalyst may be employed, it is preferred that such effective amount constitute from about 10 mole to about 300 mole percent based on the molar amount of sulfur dichloride employed, and most preferably from about 150 to about 250 mole percent of catalyst based on the molar amount of sulfur dihalide. Lower levels of catalyst can be employed and are effective, but the reaction rate generally decreases at such low levels as the catalyst level decreases.

It is preferred that no additional solvent is employed in the instant process other than the aromatic reactant compound. Thus, when the alkoxy or phenoxy aromatic reactant is a liquid at reaction temperature, same is preferably employed in an amount sufficient to fulfill the dual role of reactant and solvent, i.e., the aromatic reactant compound is employed in an amount sufficient to solvate the sulfur dihalide and catalyst sufficiently to thereby allow the reaction to proceed. The only upper limit on the amount of substituted aromatic compound would be that of a practical limit with regard to the reaction kinetics to insure that the concentrations of the sulfur dihalide and catalyst were not so minute as to adversely effect the rate of reaction or yield of product. A suitable inert hydrocarbon or halocarbon solvent may be employed, however, and when the aromatic reactant compound is a solid at the reaction temperature, an inert hydrocarbon or halocarbon solvent is used as the sole solvent.

Although any such sufficient amount of aromatic reactant is suitable, generally, when the aromatic compound fulfills the dual role of solvent and reactant, the amount of aromatic compound employed is such that the molar ratio of aromatic compound to sulfur dihalide is in the range of about 2:1 to about 50:1, which has been found to be sufficient for achieving good results. Even more preferable is a molar ratio in the range of about 4:1 to about 25:1.

In conducting the reaction, the molar ratio of the aromatic reactant compound to the sulfur dihalide reactant will determine the type of product obtained. Oligomers are obtained when a molar ratio of greater than 1:1 and less than 2:1 is employed, with the closer the molar ratio being to 2:1 the less aryl units in the oligomer. Thus, when an oligomer is the desired product, a suitable inert solvent is generally employed in order that the aromatic reactant to sulfur dihalide molar ratio not exceed 2:1. Dimeric products, i.e., diaryl sulfides, are prepared when a molar ratio of at least 2:1 is employed.

The reaction can be conducted in any suitable reaction vessel which can be maintained free of water or water vapor. This is to avoid the deleterious reaction of the sulfur dihalide with water, as sulfur dichloride, for example, is very reactive to water in any form. The reaction vessel is also preferably equipped with a conventional stirrer as the reaction is preferably run under agitation. Hydrogen chloride gas is evolved as a by-product of the reaction, thus, in commercial operations where recovery of said hydrogen chloride by-product gas is desired, the reaction can be conducted in a vessel equipped with suitable recovery means. Furthermore, an inert gas sweep, e.g., employing gases such as nitrogen, argon, etc., can be used to aid in removing the hydrogen chloride gas evolved.

The addition of the aromatic compound and sulfur dihalide reactants and alkali metal tetrafluoroborate catalyst to the reaction vessel need be in no particular order. It is preferred, however, to dissolve and/or suspend the tetrafluoroborate catalyst in the aromatic reactant/solvent, and then add the sulfur dihalide slowly thereto, preferably dropwise.

The reaction temperature, if so desired, may be monitored by any conventional means, e.g., a thermocouple. The reaction temperature employed can be any effective temperature, but is preferably below about 110° C. due to the low boiling point of sulfur dihalides, e.g., sulfur dichloride (ca. 60° C.). Thus, it is preferred that the reaction temperature employed generally be in the range of about 0° to 110° C., more preferably in the range of about 25° C. [about ambient temperature] to about 100° C., and most preferably in the range of about 35° to about 90° C.

One of the major advantages of the instant process is the fast reaction rate achieved through the use of the alkali metal tetrafluoroborate catalyst. The time for the reaction to run to completion, of course, will vary depending on the temperature conditions employed, concentration of the reactants and catalyst, and the particular catalyst and reactants employed. Generally, however, the reaction is cmpleted in less than about 10 hours. Completion of the reaction with excellent yields has also been achieved, however, in reaction times of less than about five hours, e.g., from two to five hours, Therefore, the reaction time employed is generally in the range from about 1 to about 10 hours, and most preferably in the range of about two to about five hours.

If so desired, the reaction temperature need not remain the same throughout the reaction. Rather, the reaction temperature can be sequentially raised so that the reaction is conducted for predetermined periods of time at several different temperatures. Due to the high reaction rates achieved by the instant process, however, the total reaction time is still generally less than 10 hours, and still preferably in the range of about two to about five hours.

Once the reaction has run to completion, water can be added to the reaction product mixture in order to separate the catalyst and residual hydrogen chloride from the desired aryl sulfide product. The catalyst can be recovered from the water by conventional techniques. Excess solvent and/or aromatic reactant can be removed via distillation.

The solid substituted aryl sulfide product can then be further purified by washing with a suitable wash solution, e.g., a sodium carbonate or sodium hydroxide solution. This washing should remove all remaining traces of by-product hydrogen chloride. Other conventional recovery and purification techniques might also be employed. Depending on the solubility of the specific aryl sulfide product, conventional concentration techniques might be suitably employed. For example, recrystallization from a low molecular weight alcohol such as ethanol.

The diaryl and oligomeric substituted aryl sulfide products obtained via the instant invention find particular applicability as stabilizers and/or plasticizers. The substituted aryl sulfides also find utility as precursors for the corresponding sulfoxides and sulfones.

The following examples are given as specific illustrations of the instant invention. It should be understood, however, that the specific details set forth in the examples are merely illustrative and in nowise limitative. All parts and percentages in the examples and the remainder of the specification are by weight unless otherwise specified.

EXAMPLE I

This example illustrates the operability of the instant process for preparing 4,4'-dimethoxydiphenyl sulfide from anisole.

A multi-necked flask is immersed in a water bath which controls the flask temperature from $-10°$ to 90° C. as desired. The flask is fitted with an inert gas (argon) tube, a glass thermowell containing a thermocouple for continuously monitoring the temperature, a stirrer shaft and blade, a condenser fitted with a drying agent protective tube, and an addition tube. To the flask is added 946 ml (8.7 moles) of anisole and 109 g (0.99 mole) of sodium tetrafluorobarate. The suspension is sparged and raised in temeprature to 40° C. while 46.4 g (0.45 mole) of sulfur dichloride is charged to the addition tube. The sulfur dichloride is then added to the flask over the next 2.5 hr. Over the next 0.5 hr. the temperature is increased to 60° C. and evolution of hydrogen chloride observed. Over the next hour the temperature is raised to and held at 80° C. during which time evolution of hydrogen chloride continues. The reaction mass is then cooled, extracted with water, washed with 5% sodium carbonate solution, and treated in vacuo to remove unreacted anisole yielding 77.2 g, 69.6% of theory, of 4,4'-dimethoxydiphenyl sulfide whose structure and purity are confirmed by Fourier Transform IR and proton NMR.

EXAMPLE II

Using the same general procedure as in Example I, 500 ml (3.15 moles) of diphenyl ether are reacted with 78.8 g (0.766 mole) of sulfur dichloride in the presence of 184.9 g (1.64 moles) of sodium tetrafluoroborate. Upon removal of unreacted diphenyl ether, 207 g of 4,4'-diphenoxydiphenyl sulfide (73% of theory) are obtained.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed:

1. A process for the synthesis of a alkoxy or phenoxy substituted aryl sulfide comprising reacting in the presence of a catalytic amount of an alkali metal tetrafluoroborate catalyst a sulfur dihalide with an aromatic reactant compound of the structural formula

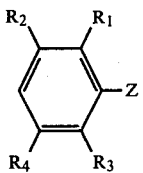

wherein $R_1$, $R_2$, $R_3$ and $R_4$, which can be the same or different, represent hydrogen or a lower alkyl, and Z is —$OR_5$ with $R_5$ representing an alkyl having from 1 to 8 carbon atoms or a phenyl.

2. The process of claim 1 wherein said aromatic reactant compound is employed in an amount sufficient to solvate said sulfur dihalide and catalyst sufficiently to allow said reacting to occur.

3. The process of claim 1 wherein the aryl sulfide is a diaryl sulfide.

4. The process of claim 1 or 3 wherein the sulfur dihalide is sulfur dichloride.

5. The process of claim 2 or 3 wherein said aromatic reactant compound is anisole and the aryl sulfide formed is 4,4'-dimethoxydiphenyl sulfide.

6. The process of claim 2 or 3 wherein said aromatic reactant compound is diphenyl ether and the aryl sulfide formed is 4,4'-diphenoxydiphenyl sulfide.

7. The process of claim 1 or 2 wherein said catalyst is selected from the group consisting of lithium tetrafluoroborate and sodium tetrafluoroborate.

8. The process of claim 1 or 2 wherein said catalyst is sodium tetrafluoroborate.

9. The process of claim 1 or 2 wherein the mole ratio of the aromatic compound to sulfur dihalide is in the range of about 2:1 to about 50:1, and the amount of catalyst employed is from 10 mole to about 300 mole percent based on the molar amount of sulfur dihalide.

10. The process of claim 9 wherein said mole ratio of aromatic compound to sulfur dihalide is in the range of about 4:1 to about 25:1, and said molar amount of catalyst based on the amount of sulfur dihalide is from about 150 to about 250 mole percent.

11. The process of claim 1 or 2 wherein said reaction is conducted at a temperature in the range of about 0° to 110° C. for a period of time ranging from about 1 to about 10 hours.

12. The process of claim 11 wherein said reaction temperature is in the range of about 35° to 90° C. and said period of time ranges from about two to about five hours.

13. The process of claim 5 wherein the sulfur dihalide comprises sulfur dichloride and the mole ratio of the aromatic compound to sulfur dichloride is in the range of from about 4:1 to about 25:1, said catalyst is sodium tetrafluoroborate and is employed in an amount ranging from about 150 to about 250 mole percent based on the amount of sulfur dichloride, and wherein said reaction is conducted at a temperature in the range of about 35° to 90° C. and for a period of time ranging from 1 to about 10 hours.

14. The process of claim 1 or 2 wherein the aryl sulfide is an oligomer.

15. The process of claim 14 wherein the mole ratio of the aromatic compound to sulfur dihalide is greater than 1:1 but less than about 2:1 and the amount of catalyst employed is from 10 to about 300 mole percent based on the molar amount of sulfur dihalide.

16. The process of claim 14 wherein the sulfur dihalide is sulfur dichloride.

17. The process of claim 15 wherein the sulfur dihalide is sulfur dichloride.

* * * * *